United States Patent
Laubstein (12)

(10) Patent No.: US 9,435,717 B2
(45) Date of Patent: Sep. 6, 2016

(54) DEVICE FOR MANUAL FINE METERING, AND SCALE

(71) Applicant: Sartorius Lab Instruments GmbH & Co. KG, Goettingen (DE)

(72) Inventor: Michael Laubstein, Goettingen (DE)

(73) Assignee: Sartorius Lab Instruments GmbH & Co. KG, Goettingen (DE)

( * ) Notice: Subject to any disclaimer, the term of this patent is extended or adjusted under 35 U.S.C. 154(b) by 450 days.

(21) Appl. No.: 13/957,130

(22) Filed: Aug. 1, 2013

(65) Prior Publication Data

US 2014/0000390 A1    Jan. 2, 2014

Related U.S. Application Data

(63) Continuation of application No. PCT/EP2011/005955, filed on Nov. 26, 2011.

(30) Foreign Application Priority Data

Feb. 1, 2011    (DE) .................. 10 2011 000 433

(51) Int. Cl.
| | |
|---|---|
| *G01N 1/20* | (2006.01) |
| *B01L 3/02* | (2006.01) |
| *G01G 13/02* | (2006.01) |
| *G01G 23/00* | (2006.01) |

(52) U.S. Cl.
CPC ................ *G01N 1/20* (2013.01); *B01L 3/021* (2013.01); *G01G 13/02* (2013.01); *G01G 23/00* (2013.01); *B01L 2200/0657* (2013.01)

(58) Field of Classification Search
CPC ............................. G01N 1/20; G01N 1/2035
USPC ...................................................... 73/863.44
See application file for complete search history.

(56) References Cited

U.S. PATENT DOCUMENTS 5,870,961  A    2/1999  Morin

FOREIGN PATENT DOCUMENTS

| CH | 681148 A5 | 1/1993 |
|---|---|---|
| DE | 256186 A1 | 4/1988 |
| EP | 2072974 A1 | 6/2009 |
| GB | 2440443 A | 1/2008 |
| KR | 100857308 B1 | 9/2008 |

*Primary Examiner* — Hezron E Williams
*Assistant Examiner* — Rodney T Frank
(74) *Attorney, Agent, or Firm* — Edell, Shapiro & Finnan, LLC

(57) ABSTRACT

A device for manual fine metering of a substance, in particular in powder form, provided with a manual transport tool (24), also having a movable part (32) configured to be induced to vibrate by a motor and wherein the transport tool (24) is held against the movable part (32) in order to induce the transport tool (24) to vibrate. An electronic scale (10) provided with a device of this type enables better manual metering.

16 Claims, 1 Drawing Sheet

DEVICE FOR MANUAL FINE METERING, AND SCALE

The present application is a Bypass Continuation of International Application No. PCT/EP2011/005955, filed on Nov. 26, 2011, which claims priority from German Patent Application No. 10 2011 000 433.5, filed on Feb. 1, 2011. The contents of these applications are hereby incorporated into the present application by reference in their respective entireties.

FIELD AND BACKGROUND OF THE INVENTION

The invention relates to a device for manual fine metering of a substance, particularly in powder form, from a manual transport tool. The invention also relates to a scale with a corresponding device.

In laboratories of the chemical and pharmaceutical industries and for research purposes, very small samples of substances are used for the analysis of such substances. Sample quantities in the range of 1 mg to 50 mg are very common. The samples are often manufactured only once, so that automatic metering heads are not suitable. For manual fine metering, use is made of a high-resolution scale, onto the receiving container (for example, scale pan) of which the substance is poured utilizing a transport tool until the desired mass has been placed on the receiving container. The transport tool is typically a spatula which can easily be tipped, tapped or shaken over the receiving container of the scale so that small quantities of the substance fall from the spatula. Using this metering method which is commonplace in laboratories, it is often the case that metering accuracies of only 10% are achieved.

A device for automatic, that is, not for manual, metering is disclosed by EP 2 072 974 A1. Herein, powder is automatically poured out of a container into a vibrating funnel, from where the powder enters a container which has a small filling opening.

Vibrating spatulas are also known, in which a vibrating element is accommodated in the handle of the spatula, causing the spatula tip to vibrate and thus assisting with metering. The resulting large handle proves to be unwieldy for handling samples in the mg range.

OBJECTS AND SUMMARY OF THE INVENTION

It is an object of the invention to provide a device for manual fine metering which enables more rapid and, in particular, substantially more accurate metering of substances, in particular powdered substances, from a manual transport tool.

According to one formulation, this object is achieved with a device of the aforementioned type having a movable part, against which the transport tool is movable, and which is externally closed and is coupled to a vibration exciter and is capable of being induced to vibrate by the vibration exciter, wherein the transport tool vibrates on contact with the vibration exciter. The transport tool can be pressed against the movable part via the inventive device, wherein the transport tool is induced to vibrate by the vibrating part. These small vibrations are precisely pre-determinable so that tipping or tapping of the transport tool is no longer necessary in order to make the substance fall off the tool. The speed of metering is also substantially greater than would be possible when performed purely manually. The vibrating part is arranged in the portion accessible from outside, that is, in the portion of the device which is contactable by the transport tool, the device being a body closed in relation to the exterior. This means that the vibrating part does not perform the metering because the substance to be metered does not fall through this part, as would be the case with a funnel, a container or the like. Furthermore, as a result of the surface closed to the exterior, none of the substance remains adhering to the movable part.

The vibration exciter is electrically powered and has, for example, a piezoelectric drive or an electric motor.

The device is arranged, in particular, in a closed, mobile unit, simply placed on a mounting (in particular a windshield of a weighing chamber) and can be removed again therefrom without any tools or fasteners being required therefor.

The vibration exciter is coupled to a switch for switching on and off, wherein in the simplest embodiment of the vibration exciter, switching on and off can be achieved with a switch, wherein a standby mode is also possible.

However, in a preferred embodiment, a sensor is provided which detects the presence of the transport tool close to the moving part and initiates the switching on of the vibration exciter. The vibration exciter is also not configured to be permanently active, but only when the transport tool is close thereto. This is also advantageous because, in this way, the operator can concentrate entirely on the metering and does not additionally have to actuate switches for switching the vibration exciter on and off. Furthermore, in the case of high-resolution scales, permanent vibration could falsify the measuring result.

A sensor of this type can be, for example, an optical sensor.

An alternative embodiment of the sensor provides that the sensor is configured as a contact sensor which detects contact or deflection of the movable part by the transport tool and initiates switching on of the motor. Above all, this embodiment can be implemented in a very simple technical manner. The operator simply presses against the movable part, which closes a contact and switches the vibration exciter on.

A circuit as part of the device can be configured so that the vibration exciter is moved for as long as the transport tool is situated close to, touches or deflects, the movable part.

Furthermore, a time switch can be provided which causes the vibration exciter to run for a fixed time period following an excitation thereof.

It is advantageous for the frequency and/or the amplitude of the vibrations to be adjustable in order to also be able to adapt these variables in an optimum manner to the type of substance.

The device should preferably comprise a housing which, in particular, is enclosed in order to prevent the contamination of the housing interior by the substances. The movable part projects out of the housing.

Particularly with regard to the avoidance of contamination, it is advantageous if the part is mounted to be exchangeable in relation to the remainder of the device, in particular released, simply by pulling it out from the device without the use of a tool, and to be reattached thereto by insertion.

According to a preferred embodiment, the movable part is elongate, for example, a rod, in particular a cylindrical metal rod which is as smooth as possible.

The mounting of the movable part is preferably elastic.

The elastic mounting preferably also forms a seal of the housing around the movable part so that the elastic mounting has a double function. In the simplest embodiment, the movable part is simply inserted into a type of rubber ring which secures the movable part against falling out and also supports the part laterally.

The device can also be exchanged from one workstation to another or can be installed if the device is battery powered.

Typical use of the device according to the invention involves it being placed on a container or on an opening of a chamber. The movable part thus extends into the chamber and the remainder of the device remains outside thereof. The chamber is, in particular, a weighing chamber which is closed by a windshield. The device therefore forms part of the cover or the entire cover of the windshield.

The base of the housing is provided, in particular, with vibration isolation, for example, an elastic layer which provides both for vibration decoupling and for sealing.

The invention also relates to an electronic scale having an inventive device which is positioned above a scale pan. In operation, the device is preferably releasably or removably coupled to the scale so that the device is positioned in a particular, spatially fixed manner.

The device can be coupled to the scale such that, on reaching a pre-determined mass of the substance to be metered, the motor is switched off. This provides for highly accurate metering.

BRIEF DESCRIPTION OF THE DRAWINGS

Further features and advantages of the invention are disclosed in the following description and the accompanying drawings to which reference is made and in which.

DETAILED DESCRIPTION OF EXEMPLARY EMBODIMENTS

Figure 1:
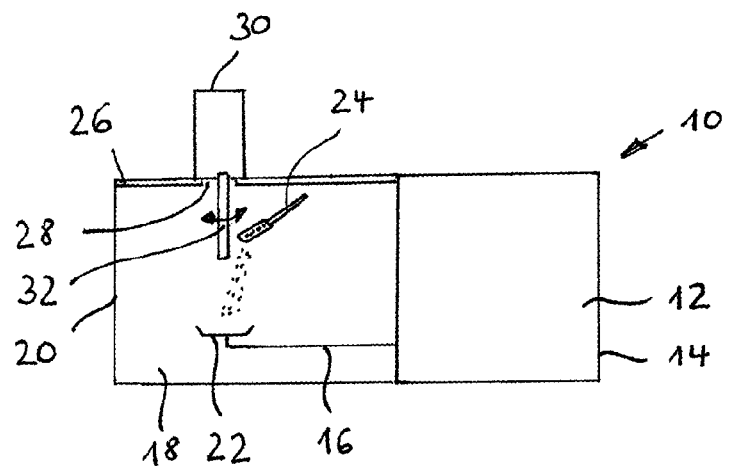
FIG. 1 is a side view of an inventive scale having an inventive metering device.

FIG. 1 shows an electronic scale 10 which comprises a weighing system 12 which is enclosed by a housing 14 and on which a load boom arm 16 is mounted. This load boom arm 16 projects out of the housing 14 into a weighing chamber 18 which is delimited by a windshield 20. The windshield 20 can be opened laterally in order to introduce the goods to be weighed into the weighing chamber 18 and to meter these goods onto a pan 22 at the load boom arm 16. Naturally, a container can also be placed on the pan 22, into which the substance to be metered is placed.

High-resolution scales of this type are used, as already stated above, particularly in laboratories in the chemical and pharmaceutical industries and in research departments. The metering of substances must therefore be carried out highly precisely, particularly since sample quantities of sometimes only 1 mg have to be weighed out.

The substances are manually introduced into the weighing chamber 18 and metered with a transport tool 24. Typically, the transport tool 24 is a spatula which has a channel-shaped end on which a very small quantity of a powdered substance is transported.

The upper wall 26 of the windshield 20 has an aperture 28 into which a device for manual fine metering extends. This device has a housing 30 arranged outside the weighing chamber and a movable part 32 extending out of the housing 30 and vertically from above into the weighing chamber 18.

The movable part 32 is externally closed in the region in which the part projects out of the housing 30, that is, this part has no undercut or aperture.

In the exemplary embodiment shown, the movable part 32 is a cylindrical elongate rod made, in particular, of metal.

The housing 30 seals the aperture 28, preferably in a dust-proof manner.

The device is removable, that is, the device is preferably only placed on the wall 26 and can be removed without disassembly and used with another scale.

According to a preferred embodiment, the device is energy-independent in relation to the exterior, being battery-powered, as described below. This extends the range of uses for the device.

The movable part 32 can be induced to vibrate, as will also be described in greater detail below, such that the transport tool 24 is also induced to vibrate when pressed laterally against the vibrating part 32. In this way, small quantities of substances are made to fall off the tool 24, in a very finely metered manner.

As FIG. 1 shows, the movable part 32 is arranged oriented toward the pan 22, preferably centrally thereto.

Figure 2:
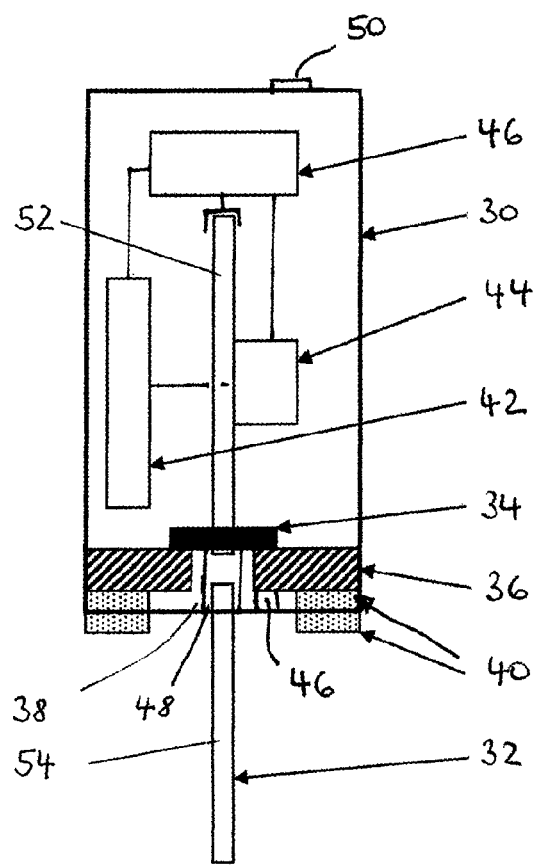
FIG. 2 is a schematic sectional view through an inventive metering device.

The design of the device according to the preferred embodiment of the invention is shown in greater detail in FIG. 2. The rod-shaped movable part 32 extends into the housing 30 and is held in the axial and radial direction by an elastic bearing 34, for example, in the form of an elastomer ring. Preferably only one mounting site is provided, arranged between the ends in the central section of the part 32.

The bearing 34 in which the part 32 is mounted also represents a seal of the housing 30 downwardly.

A support 36 provides a base or even the floor of the housing 30 and has an aperture 38 which is large enough to permit lateral deflection of the part 32. This aperture 38 is closed upwardly by the bearing 34 which is fastened to the support 36, for example, by gluing.

In order to achieve vibration decoupling of the device relative to the wall 26, a vibration isolation 40 can be provided, for example, in the form of elastomer disks, within or externally to the housing 30 in the region of the floor thereof. The vibration isolation 40 arranged externally to the housing 30, shown here in the form of rings, is arranged at the edge of the wall 26 around the aperture 28 and also acts as a seal.

Arranged in the interior of the housing 30 is a battery 42 which is configured to be rechargeable. This battery 42 is connected to a vibration exciter 44 which is also linked to the movable part 32.

The preferred embodiment of a vibration exciter 44 of this type is a motor which is out of balance.

A circuit provided in the housing 30, symbolized by the connecting lines, also has one or more sensors 46.

In the simplest case, the sensor 46 is a switch which is connected to the part 32 and which detects a lateral deflection of the part 32. Furthermore, touch sensors 46 can be effectively utilized.

The part 32 comprises two sections which suitably can be detachably connected to one another at a coupling site 48, specifically an upper part 52, which is permanently connected to the sensor 46 and the vibration exciter 44, and an exchangeable lower part 54.

Furthermore, however, the sensor 46 can also be a contact-free sensor, for example a Reed sensor, which also detects a lateral deflection of the movable part 32. Optical sensors for position recognition are naturally also possible.

Furthermore, a sensor 46 can also be attached to the lower end wall of the housing 30 and detect the presence of the tool 24.

The purpose of the sensor 46, regardless of the design thereof, lies in detecting the presence of the tool 24 for the purpose of switching on the electrical vibration exciter.

In one embodiment, it is provided that, on touching or exerting slight lateral pressure against the part 32 by the tool 24, the sensor 46 detects this contact or deflection and, through operation of the circuit, the vibration exciter 44 is switched on.

The vibration exciter 44 can run for as long as the tool 24 makes contact or for a fixed duration (time switching). Thereafter, the vibration exciter 44 is switched off again.

It is, however, also possible to couple the device to the scale 10 for control purposes, this coupling taking place via a wireless or cable connection. The vibration exciter 44 runs until a pre-determined mass of the substance to be metered is reached. This enormously simplifies and also accelerates the metering.

A simplified embodiment of the invention provides for actuation of the device or switching of the device into standby mode with an external switch, wherein the switch could be mounted at the device or at the scale.

The frequency and/or amplitude of the vibrations are adjustable, for example, by adjusting elements 50 mounted at the housing 30.

Since, during metering, particles could remain adhering to the part 32 and contaminate the next sample, the lower part 54 of the part 32 is exchangeably mounted in the coupling site 48. Without the need for a tool to be used, the lower part 54 is simply withdrawn from the coupling site 48 and is replaced with another, clean lower part 54.

The above description of various embodiments has been given by way of example. From the disclosure given, those skilled in the art will not only understand the present invention and its attendant advantages, but will also find apparent various changes and modifications to the structures and methods disclosed. The applicant seeks to cover all such changes and modifications as fall within the scope of the invention, as originally disclosed and defined by the appended claims.

The invention claimed is:

1. An electronic scale, comprising:
    a scale pan, and
    a device for manual fine metering of a substance, with a manual transport tool, comprising a vibration exciter and a movable part which is coupled to the vibration exciter and which is configured to vibrate in response to actuation by the vibration exciter, wherein the transport tool vibrates on contact with the vibration exciter.

2. The electronic scale as claimed in claim 1, wherein the device further comprises a switch for switching the vibration exciter on and off.

3. The electronic scale as claimed in claim 1, wherein the device further comprises a sensor which detects the transport tool when positioned in a given proximity to the movable part in order to initiate switching on of the vibration exciter.

4. The electronic scale as claimed in claim 3, wherein the sensor is part of a circuit which is configured such that the vibration exciter is moved for as long as the transport tool is situated close to, touches or deflects, the movable part.

5. The electronic scale as claimed in claim 3, wherein the sensor is a contact sensor which detects contact or deflection of the movable part by the transport tool in order to initiate switching on of the vibration exciter.

6. The electronic scale as claimed in claim 1, wherein the device further comprises a time switch which supplies current to the vibration exciter for a fixed time period following excitation of the vibration exciter.

7. The electronic scale as claimed in claim 1, wherein the movable part is at least one of rod-shaped and exchangeably mounted at the remainder of the device.

8. The electronic scale as claimed in claim 1, wherein at least one of a vibration frequency and a vibration amplitude of the movable part is adjustable.

9. The electronic scale as claimed in claim 1, wherein the device further comprises a housing out of which the movable part projects.

10. The electronic scale as claimed in claim 9, wherein the movable part is elastically mounted to the housing with an elastic mounting that extends around the movable part.

11. The electronic scale as claimed in claim 10, wherein the elastic mounting forms a seal of the housing around the movable part.

12. The electronic scale as claimed in claim 1, wherein the device further comprises a battery powering the device.

13. The electronic scale as claimed in claim 1, wherein the device is positioned above the scale pan.

14. The electronic scale as claimed in claim 1, further comprising a coupling configured to switch off the vibration exciter on reaching a pre-determined mass of the substance being metered.

15. The electronic scale as claimed in claim 1, wherein the device further comprises a base configured to mount said device onto an aperture of a chamber into which the movable part projects.

16. The electronic scale as claimed in claim 15, further comprising a vibration isolation member provided at the base of the device.

\* \* \* \* \*